United States Patent [19]

Girgis et al.

[11] Patent Number: 5,409,840

[45] Date of Patent: Apr. 25, 1995

[54] PURIFICATION AND RECOVERY OF LIPOPROTEIN CHOLESTEROL

[75] Inventors: Makram M. Girgis, Bradley; Thomas M. McCall, Kankakee; Joseph G. Montalto, Bradley, all of Ill.

[73] Assignee: Miles Inc., Elkhart, Ind.

[21] Appl. No.: 133,897

[22] Filed: Oct. 12, 1993

[51] Int. Cl.$^6$ .............................. G01N 1/18
[52] U.S. Cl. ........................ 436/178; 436/71; 436/177; 435/11
[58] Field of Search ............ 422/56; 436/71, 86, 436/177, 178; 435/11; 210/782, 691

[56] References Cited

U.S. PATENT DOCUMENTS

| | | | |
|---|---|---|---|
| 4,290,774 | 9/1981 | Girgis et al. | 23/230 B |
| 4,762,792 | 8/1988 | Girgis et al. | 435/244 |
| 4,883,765 | 11/1989 | Tamir et al. | 436/71 |
| 5,141,872 | 8/1992 | Tamir | 436/71 |
| 5,290,703 | 3/1994 | Hsu et al. | 436/71 |

*Primary Examiner*—Donald E. Czaja
*Assistant Examiner*—Lien Tran
*Attorney, Agent, or Firm*—Jerome L. Jeffers

[57] ABSTRACT

Disclosed is an improved process for the recovery of cholesterol rich fractions from mammalian serum or plasma. The process involves adsorbing the fraction on precipitated silica gel agglomerates which are then separated from the serum or plasma whereupon the adsorbed cholesterol rich fraction is eluted from the silica and recovered.

10 Claims, No Drawings

PURIFICATION AND RECOVERY OF LIPOPROTEIN CHOLESTEROL

BACKGROUND OF THE INVENTION

This invention relates to a method for the purification of lipoproteins in order to provide a material high in cholesterol content which is suitable for use as a cholesterol reference standard for determining the cholesterol content of body fluids.

The analytical determination of serum cholesterol levels is a useful tool in screening for coronary artery disease, diabetes mellitus, nephrosis, hepatic and thyroid diseases as well as metabolic disorders caused by endocrine disturbances. Clinical chemistry procedures designed to facilitate the determination of cholesterol levels in serum, generally involve the use of a cholesterol control reference standard which comprises human serum and certain organic salts as components. In U.S. Pat. No. 4,290,774 there is described the desirability of a cholesterol reference material which is not used in conjunction with human serum or plasma and points out the difficulties inherent in recovering complexes formed by adsorbing lipoproteins to adsorbents to form adsorbent/lipoprotein complexes. This patent describes such a procedure which involves adsorbing a lipoprotein containing substance onto a silica adsorbent, separating the absorbed lipoprotein from the excess solution, freezing and thawing the adsorbed lipoprotein, eluting the absorbed lipoprotein at a pH of from 10 to 11.5, concentrating the lipoprotein to a desired concentration, adjusting the pH to a level of from 7.0 to 10.0; adjusting the salt concentration to a level of less than 0.05M, heating the resultant to a temperature of from 50° to 100° C., adding an alkaline carbonate and alkaline earth salt to form a precipitate, removing the precipitate, adjusting the pH to a level of from 6.5 to 9.0 and recovering the purified cholesterol. The specific silica adsorbent described in this patent is Cabosil ® ultrafine silica obtainable from Cabot Corporation of Boston, Mass.

An improvement to the procedure disclosed in the '774 patent is disclosed in U.S. Pat. No. 4,762,792 which improvement involves eluting the silica adsorbed lipoprotein at a pH of from about 10 to 11.5, adjusting the salt concentration to less than about 0.05M, heating the eluted lipoprotein to a temperature of from about 50° to 100° C. for a time sufficient to increase its storage stability, whereupon the lipoprotein fraction is dialyzed against an alkaline material such as aqueous sodium carbonate, adjusting the pH from about 6.5 to 9.0 and recovering the lipoprotein cholesterol. This patent states that the silica adsorbent does not have a critical composition and describes the Cabosil ® product as well as powdered silica available under the tradename Aerosil ® 380 from the Cary Company as being suitable.

While these prior art procedures work well for the recovery of cholesterol from serum or plasma, they suffer from the disadvantage that the liquid-solid separation is, as a practical matter, limited to centrifugation; attempts at filtration have been found to be minimally successful and labor intensive. Furthermore, in order to effectively remove solubilized Aerosil ® silicates from the high pH eluate, a freeze-thaw of the eluate is required. The freeze-thaw procedures causes significant silicate precipitation. While the precipitate may be removed by centrifugation, this process is time consuming and labor intensive.

Amorphous silica, i.e. that form of $SiO_2$ which lacks a crystal structure, has been used as an adsorbent since at least as early as World War I when it was considered for use as an adsorbent in gas masks. The microparticulate silicas include pyrogenic silicas (also known as fumed silica) and silicas precipitated from aqueous solution. In the preparation of fumed silica such as the previously mentioned, Cabosil ® and Aerosil ® products, sand is vaporized at about 2000° C. On cooling, anhydrous amorphous silica powders form in the presence of a reducing agent such as coke. The amorphous silica sublimes at about 1500° C. to provide Si which is then oxidized to produce very finely divided particulate $SiO_2$. Commercially available fumed silica will typically have an average particle size in the range of from about 7 to 16nm.

Precipitated silica (also called particulate silica) is composed of aggregates of ultimate particles of colloidal size that have become linked in a gel network. Precipitated silicas, such as Sipernat ® from Degussa, are typically formed by the precipitation of pyrogenic silica from solution.

U.S. Pat. No. 5,151,872 discloses the use of fumed silica for the adsorption of lipoproteins from plasma. The patentees point out that this procedure was known before their invention but disclose the improvement of selectively desorbing HDL from the fumed silica by incubating with a detergent containing formulation.

In commonly assigned allowed application, U.S. Ser. No. 990,592, there is disclosed a method for selectively separating high density lipoprotein from blood by contacting the blood with finely divided, porous silica. The porous silica is described comprising particles of from $1\mu$ to $1000\mu$ in their longest dimension which have surface pores of from about 80 Å to 1000 Å in size. This reference illustrates the use of Vydac porous silica of $4\mu$ particle size having a pore size of 300 Å in its Example I. Microporous silica gels are obtained by heating a hydrated gel at 1000° C. for about 10 hours. The '592 application is concerned with the use of large pore silicas and silicates such as microporous silica, silica gel and controlled pore glass as selective adsorbent materials for HDL from blood serum or plasma.

SUMMARY OF THE INVENTION

The present invention involves an improved method for isolating and purifying a cholesterol rich fraction from mammalian blood serum or plasma containing cholesterol which comprises the steps of:
 (a) contacting the cholesterol containing serum or plasma with a precipitated silica to adsorb a cholesterol rich fraction of the serum or plasma;
 (b) separating the adsorbed cholesterol rich fraction from the serum or plasma sample being treated; and
 (c) eluting the adsorbed cholesterol rich fraction from the silica absorbent at a pH of from about 9.0 to 12.0 and separating the eluted cholesterol rich fraction from the adsorbent;
while maintaining the temperature of the operation within a range of from about 0° to 37° C.

DESCRIPTION OF THE INVENTION

The cholesterol source for use in the present invention can be any mammalian blood serum or plasma containing cholesterol. When plasma is used, it is normally defibrinated. Plasma used as a source for cholesterol in the present system is preferably treated in a manner capable of removing fibrinogen since the presence of this material will increase potential processing difficulties, particularly downstream filtrations. Suitable starting materials include bovine, horse, sheep, pig and human blood fractions. When the cholesterol rich fraction is to be used as a cholesterol reference standard, human serum or plasma is used. When the starting material is serum, a soluble salt is preferably added to bring the ionic strength to a level of from 0.25 to 1.0. Suitable salts include sodium citrate, sodium chloride, sodium phosphate, ammonium phosphate and sodium sulfate. Raising the ionic strength will increase the amount of cholesterol rich fraction adsorbed in the subsequent silica adsorption step.

The plasma or serum starting material is maintained at a temperature of from 0° to 37° C., preferably from 20° to 25° C. throughout the entire process. This is in contrast to prior art processes wherein the cholesterol rich solution is heated to 50° to 100° C. for a period of up to 24 hours in order to increase its storage stability.

The silica adsorbent useful in this process is a precipitated silica, prepared by precipitation from an appropriate solvent, which is typically an agglomerate of particles of the much finer fumed silica. Sipernat ® precipitated silica from Degussa, which is available in various grades having an average agglomerate size of from about 45 to 500 µm, has been used successfully in this process. The precipitated silica is typically added to the liquid serum or plasma in an amount of from 1 to 120 g/L, preferably from 60 to 100 g/L. A pH of 7.0±0.1 is preferred for this step. Adsorption can occur, however, at a pH of from about 4.0 to 8.0 when serum or defibrogenated plasma is used. It has been discovered that fibrinogen can be readily removed from blood plasma by acidifying with an acid such as HCl to a level of 3.0 to 4.5, preferably pH 4.0 to precipitate the fibrinogen with subsequent removal of the precipitate. When plasma containing fibrinogen is used, the adsorption of the cholesterol to the silica is typically carried out at a pH of from about 6.0 to 8.0 to avoid interference from fibrinogen precipitate. The silica suspension in the liquid serum or plasma is thoroughly mixed, typically for a period of up to 4 hours, to achieve complete adsorbtion.

Optionally, there may be added a polyethylene glycol such as Carbowax PEG 3350 from Union Carbide to aid in the liquid-solid phase separation of the silica absorbent from the mother liquor. This is preferably done at a pH of 6.0 or greater. The silica, having the cholesterol rich fraction adsorbed thereto, is then separated from the remaining serum or plasma, preferably by centrifugation. At this point in the procedure, the silica/cholesterol rich fraction is resuspended in water and the pH adjusted to a level of about 9.0 to 12.0, preferably 11.4 to 11.6, by the addition of an appropriate amount of base (e.g. NaOH) or acid (e.g. HCl) to elute the cholesterol rich fraction from the silica, typically by allowing the silica to settle while leaving the cholesterol rich fraction in suspension which is syphoned off for further treatment. This elution step can be repeated as often as desired and the supernatants pooled to maximize yields.

The cholesterol rich fraction is clarified by molecular filtration using a filtration membrane whose pores are sized such that molecules above a nominal molecular weight are retained. Accordingly, proper selection of the appropriate filter membrane results in retention of the cholesterol rich solution whereas the excluded fraction, i.e. the material passing across the porous membrane, contains low molecular weight peptides, salts and other unidentified low molecular weight analytes. Further purification such as by resuspension and separation by further filtration and/or centrifugation may be carried out.

The advantages of using a precipitated silica, such as Sipernat ®, over a fumed silica, such as Aerosil ®, are three-fold. They are:

1. The precipitated silica is less water soluble at high pH than the fumed silica. Accordingly, simple molecular filtration is sufficient to remove dissolved silica from the cholesterol rich fraction. Concentration of dissolved fumed silica requires the use of alkaline carbonate/alkaline earth precipitation and/or the freeze/thaw of the cholesterol rich eluate to remove excess dissolved silicates.
2. The settling characteristics of precipitated silica and filterability are superior to those of fumed silica due to its larger particle size.
3. In conjunction with the use of polyethylene glycol, there is a difference in protein adsorption selectivity between fumed and precipitated silica, i.e. there is a more rapid settling of the lipoprotein-silica complex in conjunction with the use of precipitated silica gel.

The present invention is further illustrated by the following example:

EXAMPLE I

Frozen human plasma is thawed, pooled, warmed to 25° C. and mixed with agitation for one hour. There is added 1 g of BH-40 Filter Aid Cellulose, Celite Corporation per liter of plasma and the resulting solution is clarified through a CPX-01A filter pad made by CUNO and blown dry. At this point there was added 10.5 g/L of sodium citrate to increase the ionic strength of the solution thereby aiding the adsorption of lipoprotein by the silica followed by agitation for 30 minutes to complete its solubilization whereupon there is added 10 g of polyethylene glycol (3350 mol. wt.) per liter of plasma to aid in the liquid-solid phase separation of the silica from the mother liquor followed by an additional 30 minutes of agitation. At this point in the procedure the pH is adjusted to 7.0±0.1 with /N HCl and there is added 80 g of Sipernat ® 50 silica gel per liter of plasma followed by an additional 30 minutes of agitation. Sipernat ® 50 is a precipitated silica having a BET surface area of 450 m²/g, an average agglomerate size of 50 µm and a density of 100 g/L. The pH is again adjusted to 7.0±0.1 with 1N NaOH or HCl and agitated for an additional 4 hours whereupon it is centrifuged and the supernatant checked for cholesterol content. If the cholesterol level is greater than 15 mg/dL the adsorption is carried out for an additional hour and samples are resubmitted for cholesterol determination.

A quantity of 0.02M Na Phosphate/0.15M NaCl/0.17 EDTA equal to 10.2× the starting volume of plasma is added to buffer the solution to pH 7.0. The salts are dissolved in ⅔ of the amount of purified $H_2O$ required to remove occluded proteins from the silica adsorbent whereupon the pH is adjusted to 7.0±0.1 with 1N NaOH and then q.s. to the final volume. A quantity of 0.5M $Na_2CO_3$/pH 11.5 equal to 2.0 times the starting volume of plasma is prepared and dissolved in ⅔ the volume of purified $H_2O$ required whereupon the pH is adjusted to 11.5 with 1N HCl or 1N NaOH then q.s. to the final volume. The resulting product is then centrifuged in 2 equal increments in a Fletcher Centrifuge. The precipitate is recovered and the centrifugate saved for the manufacture of delipidized serum. The precipitate is resuspended in a 1600 L tank with 1200 L of 0.02M Na Phosphate/0.15M NaCl/0.1% EDTA @ pH 7.0 and agitated for 30 minutes whereupon the suspension is allowed to gravity settle for 4 hours. The supernatant is pumped off using a rotary lobe pump and filtered through a JWI filter press using six plates without scraping until all washes are complete. The precipitate is again suspended in a 1600 L tank with 1200 L of 0.2M Na Phosphate/0.15M NaCl/0.1% EDTA, pH 7.0 buffer, agitated for 30 minutes and allowed to gravity settle for 4 hours. The supernatant is again pumped off and the recovered supernatant filtered whereupon the filter press was scraped and the precipitate added to the 1600 L tank where it is resuspended in an additional 1200 liters of the 0.02M Na Phosphate/0.15M NaCl/0.1% EDTA buffer and mixed for 30 minutes.

The resulting liquid-solid mixture of silica based adsorbent suspended in the wash buffer is centrifuged in two equal increments in the Fletcher Centrifuge to provide a paste which is scraped from the centrifuge and added to the 500 L tank and resuspended with 350 L of 0.5M $Na_2CO_3$, pH 11.5. The pH is adjusted to pH 11.5±0.1 and then equilibrated for 60 minutes followed by settling for 3 hours. The supernatant liquid is filtered through the JWI press which is precoated with 325 g of BH-40 Filter Aid and the filtrate is held for combination with the second elution which is treated in the same way. To this product is added 1 g of FW-40 diatomaceous earth from Eagle-Picher per liter of product which is filtered through Cuno housings with 05A, 30C and 60C cartridges precoated with 10 G of BH-40 Filter Aid per filter cell which postwashed with 3 liters of purified $H_2O$ per cell which washing solution was added to the product. This product is concentrated and diafiltered against 10 volumes of purified water, rinsed and drained with an additional amount of purified water and transferred to a small spiral wound molecular filtration system from Amicon Corporation where it is concentrated to 1500 mg/dL cholesterol, rinsed with 5 L of purified water and drained. The product from this step was adjusted to pH 8.2±0.1 with 1N HCl and filtered through a pre-washed cartridge housing having a 0.65µ cartridge and the resultant again filtered through a pre-washed cartridge housing equipped with a 0.2µ cartridge.

At this point the cholesterol level is adjusted to 1050 mg/dL with purified water and filtered into appropriate receiving containers through a housing containing an autoclaved Pall 0.2µ membrane.

The foregoing procedure which was carried out at normal room temperature was initially carried out with a heating step, i.e. the cholesterol rich fraction was heated to 60° C. for 10 hours. This step is called for in prior art procedures to increase the shelf life of the recovered cholesterol rich fraction by neutralizing enzymatic and microbial contamination. However, it was observed that the heating step drastically reduced the recovery of desired product when using precipitated silica as adsorbent thereby negating the advantages inherent in its use.

This loss in yield is illustrated by Table I where run 1 represents the procedure of this example and runs 2 and 3 represent the same procedure with the inclusion of the heating step.

TABLE I

| Run | Yield @ 1000 mg/dL Cholesterol | |
|---|---|---|
| | Before Heat | After Heat and Filtration |
| 1 | N/A | 29.4 (Filtered only, no heat) |
| 2 | 26L | 12L |
| 3 | 23L | 14L |
| | Starting Plasma Volume, L | Final Yield mL/L Plasma |
| 1 | 346 | 85 |
| 2 | 322 | 37 |
| 3 | 292 | 48 |

Thus, the elimination of the heating step results in dramatically improved yields of the cholesterol rich fraction. An after treatment involving the addition of a protease inhibitor such as aprotinin, and filtering the product through sterile 0.2µ filtration means, can be employed to bolster the shelf life of the material which is prepared sans the heating step.

What is claimed is:

1. A process for isolating and purifying a cholesterol rich fraction from liquid mammalian blood serum or plasma containing cholesterol consisting essentially the steps of:
   (a) contacting the cholesterol containing serum or plasma with a precipitated silica adsorbent at a pH of from about 4.0 to 8.0 to adsorb a cholesterol rich fraction of the serum or plasma;
   (b) separating the adsorbed cholesterol rich fraction from the serum or plasma;
   (c) eluting the adsorbed cholesterol-rich fraction from the precipitated silica adsorbent and separating the cholesterol rich fraction from the adsorbent by liquid solid phase separation of the precipitated silica adsorbent from the cholesterol-rich fraction at a pH of from about 9.0 to 12.0;
   (d) clarifying the separated cholesterol rich fraction by molecular filtration; and
   (e) maintaining the temperature within a range of from about 0° to 37° C. during steps a–d.

2. The process of claim 1 wherein the serum or plasma is of human origin.

3. The process of claim 2 wherein the cholesterol source is serum.

4. The process of claim 1 wherein the cholesterol source is plasma which has not been defibrogenated and the pH in step (a) is maintained at a level of from about 6.0 to 8.0.

5. The process of claim 1 wherein the temperature is maintained at a temperature of from 20° to 25° C.

6. The process of claim 1 wherein there is added polyethylene glycol to aid in the liquid-solid phase separation of the silica adsorbent from the cholesterol rich fraction.

7. The process of claim 1 wherein the eluted cholesterol rich fraction is clarified by molecular filtration.

8. The process of claim 1 wherein the precipitated silica is added to the liquid serum or plasma at a level of from 1 to 120 g/L.

9. The process of claim 8 wherein the level is 60 to 100 g/L.

10. A process for isolating and purifying a cholesterol rich fraction from human blood serum or defibrinated plasma containing cholesterol consisting essentially the steps of:

(a) contacting the cholesterol containing serum or plasma with an adsorbent of precipitated silica at a pH of about 4.0 to 8.0 to adsorb a cholesterol rich fraction of the serum or plasma;

(b) separating the adsorbed cholesterol rich fraction from the serum or plasma;

(c) eluting the adsorbed cholesterol rich fraction from the silica adsorbent at a pH of from about 9.0 to 12.0 and separating the cholesterol rich fraction from the adsorbent by a liquid-solid separation technique;

(d) clarifying the separated cholesterol rich fraction by molecular filtration; and maintaining the temperature within the range of from about 0° to 37° C. during steps a–d.

* * * * *